United States Patent [19]

Ioannides

[11] Patent Number: 4,713,964
[45] Date of Patent: Dec. 22, 1987

[54] DEVICE FOR OPTICAL TURBIDITY MEASURING OF GASES

[75] Inventor: Gregor Ioannides, Furth, Fed. Rep. of Germany

[73] Assignee: Grundig E.M.V. Elektro-Mechanische Versuchsantalt Max Grundig holland.Stiftung & Co. KG, Fuerth/Bay, Fed. Rep. of Germany

[21] Appl. No.: 887,022

[22] Filed: Jul. 16, 1986

[30] Foreign Application Priority Data

Jul. 24, 1985 [DE] Fed. Rep. of Germany ....... 3526458

[51] Int. Cl.$^4$ ........................................... G01M 15/00
[52] U.S. Cl. ....................................... 73/116; 356/439
[58] Field of Search .................... 73/118.1, 117.3, 116; 60/276; 356/408, 438, 439

[56] References Cited

U.S. PATENT DOCUMENTS 3,790,289 2/1974 Schmidt .......................... 356/438 X
4,544,273 10/1985 Berndt ............................. 356/439 X

*Primary Examiner*—Jerry W. Myracle
*Attorney, Agent, or Firm*—Kane, Dalsimer, Sullivan, Kurucz, Levy, Eisele & Richard

[57] ABSTRACT

A device for measuring the optical turbidity, i.e., the soot components in discharge gases of diesel engines, which is relatively simply constructed, operates safely and enables a simple handling even with differently structured measuring devices. This result is achieved in that a controller for controlling the light density of the measuring light beam is optically coupled with a light source. A sample and hold circuit is provided with the values of a measuring detector and the control detector fed to a sample and hold circuit in a time multiplex manner with the measuring values processed in a computer unit. Control values are fed to the light source by means of a control loop. In addition, the computer unit is capable of storing a plurality of measuring values or turbidity values and average value of the stored peak values, whereby the peak values are determined by a dynamic measuring of a defined number of measuring cycles. Moreover, a device is provided which feeds motor related parameter to the computer unit for triggering of measuring value determination and measuring value calculation.

13 Claims, 2 Drawing Figures

DEVICE FOR OPTICAL TURBIDITY MEASURING OF GASES

FIELD OF THE INVENTION

The present invention relates to a device for optical turbidity measuring of gases, in particular, for measuring soot components and the like in the exhaust of engines.

BACKGROUND OF THE INVENTION

There present exists devices and methods for measuring the soot component in exhaust gases of, in particular, diesel engines. Such devices or methods usually perform such measuring through the use of filter paper in the exhaust flow wherein the increase in weight of the filter paper or the coloration thereof caused by the soot allows for measuring the optical turbidity.

Other methods of measuring such turbidity use a light scattering method wherein the soot particles in the exhaust gas are measured. One such device is that manufactured by Berkley a.Co., Inc., Spirit Lake, Ia., U.S. under the name "Smoke Meter", Model 200. This unit operates on the principal which equates the percentage of light lost which results during an illumination of the exhaust gas. However, heretofor such known measuring devices suffer from disadvantages in particularly being hard to handle, in addition to being relatively expensive and complicated. Accordingly, there exists a need for a relatively simple, inexpensive and versatile measuring device which is effective yet allows for ease of use.

SUMMARY OF THE INVENTION

It is therefore a principal object of the present invention to provide a device for the optical turbidity measuring of gases which is relatively easily structured, operates reliably and, in addition, permits a simple handling thereof, even with variously structured outlets where such measuring may be performed.

The device taught by the invention is a relatively simply structured and economical, and allows for the determination of the turbidity in gases. Such a device is typically employed in a motor vehicle shop for testing the soot component in exhaust gases of, for example, diesel engines. The device of the present invention handles easily, and avoids the heretofor expensive test runs and measurings of previous testing methods.

The present invention teaches the use of a measuring device utilizing a controlled light emitting source across the exhaust discharge which is received by a light receiving source. The intensities of the light emitted and the light received are coupled to a sample and hold (S/H) circuit which in turn is coupled to an A/D converter. The signal for the A/D converter is sent to a microprocessor for storing a plurality of measured values and determining an average thereof and accordingly, the peak values which are determined by a dynamic measuring of a defined number of measuring cycles. The device is equipped with a control loop which adjust the amount of light emitted and thereby compensates for age or decay of the light emitting element. In addition, the device includes a triggering element which indicates when a particular engine parameter, i.e., acceleration is occurring.

BRIEF DESCRIPTION OF THE DRAWINGS

Thus by the present invention, its objects and advantages will be realized, the description of which should be taken in conjunction with the drawings, wherein.

DETAILED DESCRIPTION OF THE PREFERRED EMBODIMENT

Figure 1:
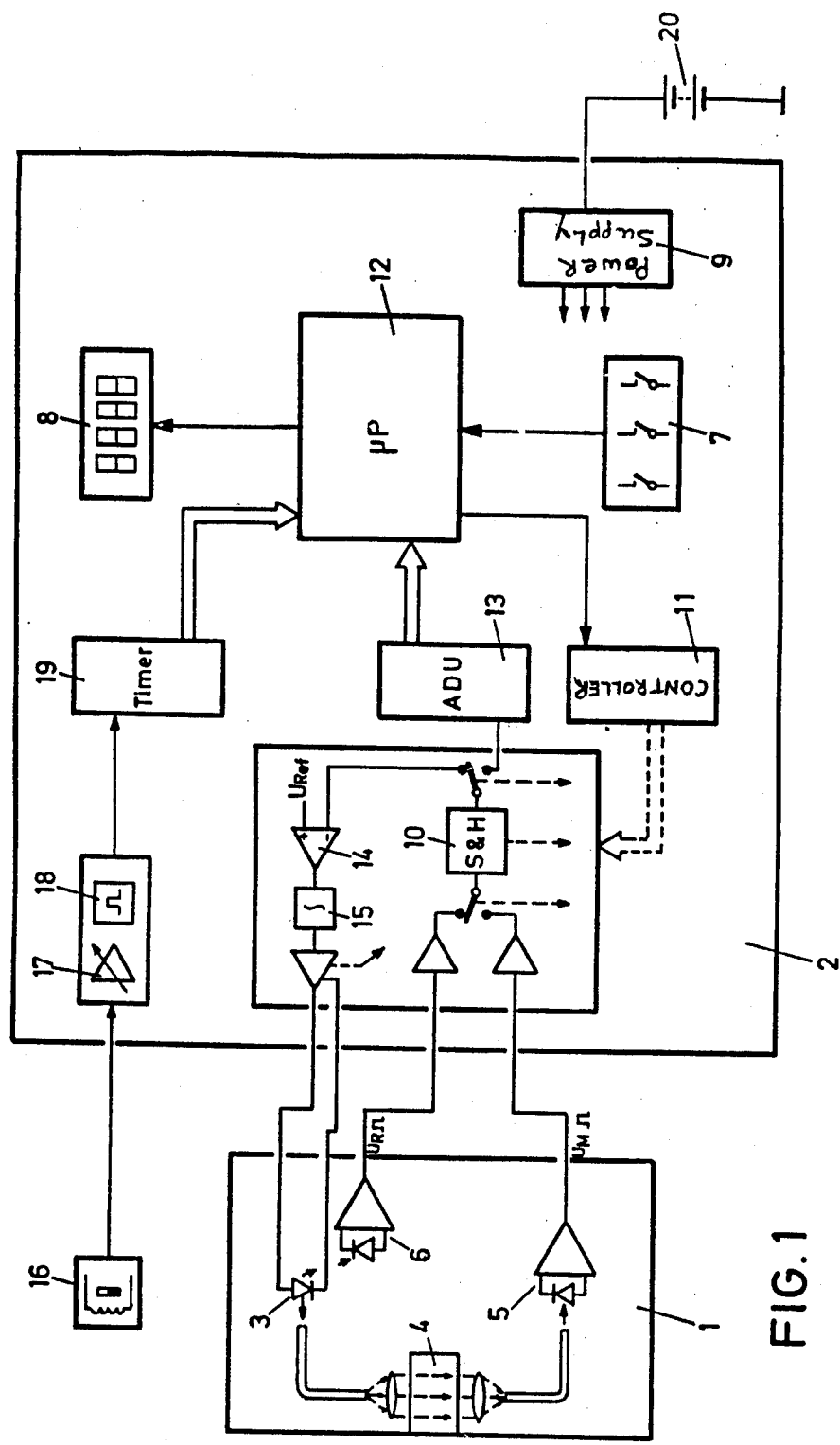
FIG. 1 is a block diagram of the measuring device incorporating the teachings of the present invention.

With reference to FIG. 1, the device in accordance with the invention consists of a measuring unit 1 and an evaluation unit 2 which may be connected via a multi-wire cable or such other type coupling, suitable for purpose.

The measuring unit 1 is intended to be a unit which is readily adaptable to be mounted on the exhaust conduit such as, in particular, the end of the exhaust pipe of a motor having a defined inner diameter and a predetermined measuring length. A detailed construction of the measuring unit 1 will be explained in more detail in conjunction with the description of FIG. 2.

Returning now to FIG. 1, the measuring unit 1 is provided with a light source 3 or light emitting means preferably in form of a light emitting diode. This light emitting diode generates light impulses of a constant density in the visible range (green), for illuminating a predetermined measuring path in a measuring chamber 4. The illumination is performed transversely with respect to the exhaust flow direction. After the light passes through the measuring path, the intensity of the light is measured by means of a light sensitive detector device 5 such as a photo sensitive diode, in a soot free condition (corresponding 0% turbidity). A reduction of the emitted light received would be caused by the soot or smoke in the exhaust. The photo sensitive diode of the receiving device 5 supplies output signals having an amplitude that is proportional to the amount of light received through in the measuring path.

A second detector or control receiver 6 is provided and includes a photo sensitive diode which is optically coupled directly with the light emitting diode 3 for controlling the light density of the light emitted.

The evaluation unit 2 which may be mounted in the driver's compartment comprises a servicing part 7, an indication unit 8 (i.e., digital indicator), and a power supply 9 as well as the electronics for signal processing, as will be discussed.

In order to eliminate expensive test drives and measurings on a roller or efficiency test stand, the process of gradual acceleration is utilized. During the dynamic measuring, the rotating mass of the motor may advantageously be used as a load. Starting from the idling running of the engine, a defined number of measuring cycles are performed which are being triggered by emitting gas thrusts from the engine, wherein the maximum blackening of the exhaust is measured. The relative light absorption of the soot particle in the exhaust gas are photometrically evaluated.

The output impulses emitted from the detection 5 and the control detector 6 of the measuring unit 1 are fed in time multiplexed fashion to a S/H circuit 10 within the evaluation unit 2. Timing is regulated by a control unit 11, in accordance with signals received from of a computer unit or microprocessor 12. The signal corresponding to the measured light is converted by an analog/-digital converter 13 and fed to the computer unit 12. In addition, control values are fed to the light source 3 through a control loop when the switches coupled to the sample and hold circuit 10 are in their up position. The signal of the control detector 6 which corresponds to the amount of light emitted by the light diode 3 is compared with a constant reference voltage $U_{Ref}$ in a comparator 14. The differential or output signal of the comparator controls the power source in conjunction with an integrator 15 in such a manner that should the light intensity of the light emitting diode decrease (a normal effect due to temperature and the aging of the light diode 3), the power source is measured thereby keeping the output of $LED^3$ constant.

In addition, measuring value determination and measuring value calculation may be performed depending upon certain motor related parameters, such as a defined speed increase of the engine or a defined increase of the soot component. In this regard, for monitoring a speed increase of the engine, transmitter 16 is connected with the evaluation unit 2. The output signal of the transmitter 16 has a frequency that is proportional to the speed of the engine. This signal is then amplified by a variable amplifier 17 and coupled with an integrator 18. The signal from the integrator 18 in turn controls a timer or clock 19 connected with the microprocessor 12 and thereby supplying the speed informations thereto.

The microprocessor 12 and peripheral device controls the total operation of the measuring device. It allows only accurate measuring methods and a monitoring of the signal transmitted. Also, the determined measuring criteria, like the defined speed or soot component increase, the storing of a plurality of measured values or turbidity peak values with maximum value determination and average value of the stored peak values as well as the measuring cycles are monitored. A control of the light intensity at diode 3 and status indications as well as manual control the calculating of the measuring values and the average value are also performed by the microprocessor unit 12.

The microprocessor 12 also provides for the simple handling of the device in accordance with the invention. A user can be guided by the measured performance. Requests to the operator, indications of the condition of the measuring device, waiting periods, measuring process, etc., may all be controlled by the microprocessor.

Turning now to the servicing selection part 7, one selects the appropriate section before each measuring process is performed. For example, a selection may be made to have measuring operation performed through the speed increase, or the increase in the soot component. Selection may be performed by way of activating appropriate keys or switches in the servicing part or manual control means 7 for the particular operation to be performed.

The measuring process serves to provide the user information and error indications as are desired. This allows for a measuring device which delivers simple and reliable measuring and excludes error source. The measuring of the soot particle concentration in the exhaust gas delivers a reliable and exact indication about the condition of the engine, so that, for example, a correct setting of the injection pump is obtained. Such data not only provides important values for measures to reduce the environmental contamination (high component of soot particles), but also allows for increasing the engine lifespan. In this regard a high component of soot particles is an indication of fuel injection amounts which are too high resulting in increased consumption and coking of the injection nozzles, thus reducing the lifespan of the engine. By a correct adjusting of the injection pump these consequences, which are damaging to the engine, are eliminated.

Figure 2:
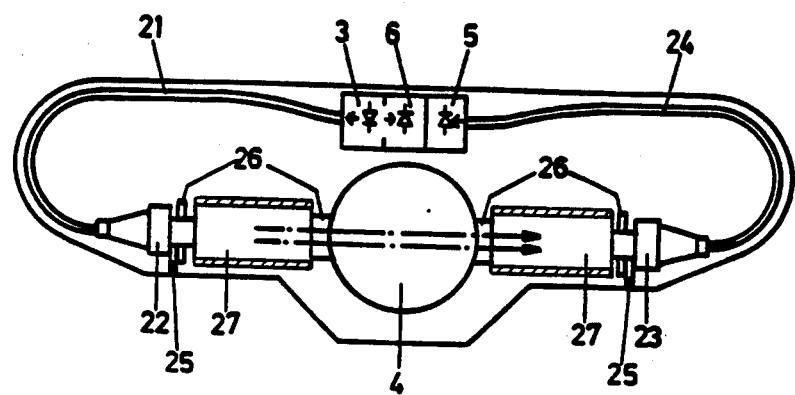
FIG. 2 is a front schematic illustration of the measuring unit for coupling to an engine exhaust, incorporating the teachings of the present invention.

With reference more particularly to FIG. 2, there is schematically illustrated the structure of the measuring unit 1 in accordance with the invention. The light diode 3 is shown as the light source along with the control detection 6 and the measuring detection 5 which together form a structural unit. The light impulses of the light diode 3 are fed through a lightwave conductor or fiber optic line 21 to an optical lens system 22 which sends a parallel bundle of rays through the measuring chamber 4 with a defined diameter.

A second optical lens system 23 collects the received bundle of rays passing through chamber 4 and a second lightwave conductor for fiber optic line 24 feeds the light to the photo sensitized diode of the measuring receiver 5. The diode 5 serves as a measuring receiver in conjunction with a transimpedance amplifier and converts the light impulses into proportional voltage impulses $U_{Mn}$, whose amplitudes are evaluated in the evaluation unit 2.

The control receiver 6 which is similarly structured detects the light which is emitted directly from the transmitter light diode 3. Its output impulses $U_{Rn}$ are proportional to the light density of the light received and serves to regulate the operating power of the transmitter diode 3. Thus, a constant light density is obtained, independent from the temperature effect and aging of the transmitter diode.

The transmitting and receiving elements are mounted in a metal block which provides the thermal uniformity and also reproducible optical conditions. Together with the lightwave conductor lines which are mounted on the block, an easily exchangeable operational block is provided.

The optical lens systems 22 and 23 are preferably heated so as to prevent dew effects. This may be by annular like PTC-resistor (cold conductor) or any other means suitable for purpose. Bores 25 in the proximity of the lens system 22 and 23 provide a suitable air flow for preventing an undue contamination by soot particles. The lenses are easily exchangeable for cleaning purposes. When contaminations of, for example, more than 20% turbidity occur a measuring by the evaluation unit 2 is prevented; the indicator unit 8 may then be signalled to optically indicate to the operator that the lenses have to be cleaned.

The structure of the measuring unit 1, in accordance with FIG. 2 is provided with shutters 26 before and after bores 25 of the arrangement are designed as light conduits with an air rinsing system.

For the housing a die cast metal part is provided for the measuring unit 1 having the optic, lightwave conductor connection and opto-electrical transmitting and receiving elements as well as the associated electronic adapter circuits. As for the measuring chamber (measuring tube) and the adaption parts for mounting the exhaust end pipe they are preferably made of steel plate. The adaptation to the exhaust pipe may be made by means of a suitable slip on nozzle made of rubber.

Thus by the aforenoted invention, its object and advantages and others will be realized, and although a preferred embodiment has been disclosed and described in detail, its scope should not be limited thereby, rather its scope should be determined by that of the appended claims.

What is claimed is:

1. A device for measuring the soot content of gases discharged by diesel engines comprising:
   a chamber disposed in a flow of gases discharging from said engine;
   a light source for projecting light through said chamber;
   a light sensor disposed opposite said light source for generating a signal corresponding to the intensity of light passing from said source through said chamber; and
   signal processing means for processing said signal and generating output signals indicative of said soot content, said signal processing means including means for storing a plurality of signals from the light sensor and determining the average and peak values of said signals for a predetermined number of said signals.

2. The device in accordance with claim 1 wherein at least one of said signals from the light sensor is generated when there is no soot content in the chamber.

3. The device in accordance with claim 2 which includes means for signalling the signal processing means to make said soot value determination when certain engine parameters exist.

4. The device in accordance with claim 3 which includes control means for controlling the light intensity of the light source, said control means includes a control loop comprising a second light sensor for monitoring the light projected by the light source and generating a signal output which is compared to a reference signal, with power to the light source adjusted in accordance with such comparison.

5. The device in accordance with claim 4, wherein said control means converts said signals from said first and second light sensors into voltage signals which are fed to an S/H circuit and in turn used to control the light output of the light source.

6. The device in accordance with claim 4 wherein said connecting means includes an electrical cable.

7. The device in accordance with claim 3 wherein upon an increase in the engine speed or increase in soot content the signal processing means makes value determinations.

8. The device in accordance with claim 7 which includes transmitter means coupled to the signal processing means to provide said latter means with the speed at which said engine is operating.

9. The device in accordance with claims 1 or 4 wherein said chamber, light source and light sensor comprise a measuring unit which is adapted to be mounted on a discharge conduit of an engine and said signal processing means is coupled with said measuring means by a connecting means.

10. The device in accordance with claim 9 where said light source and light sensor are coupled to said chamber by way of respective optical connectors.

11. The device in accordance with claim 10 which includes respective lens systems having optical lens means, shutter means and air conduit means respectively positioned on opposite sides of the chamber and to which said respective optical connectors are coupled.

12. The device in accordance with claim 11 which includes heating means for heating said lens system.

13. The device in accordance with claim 1 wherein said light source is a light emitting diode capable of emitting light at a constant density in the visible range.

* * * * *